US012751771B2

(12) United States Patent
Yoshida et al.

(10) Patent No.: US 12,751,771 B2
(45) Date of Patent: Oct. 6, 2026

(54) X-RAY DIAGNOSTIC APPARATUS, X-RAY DIAGNOSTIC SYSTEM, AND X-RAY DIAGNOSTIC METHOD

(71) Applicant: CANON KABUSHIKI KAISHA, Tokyo (JP)

(72) Inventors: Saki Yoshida, Shimoda (JP); Yoshiteru Kobayashi, Sakura (JP); Kazuo Imagawa, Nasushiobara (JP); Takuya Aida, Nasushiobara (JP); Mizuki Satoh, Nasushiobara (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 235 days.

(21) Appl. No.: 18/442,299

(22) Filed: Feb. 15, 2024

(65) Prior Publication Data

US 2024/0268895 A1 Aug. 15, 2024

(30) Foreign Application Priority Data

Feb. 15, 2023 (JP) ................................ 2023-021565
Feb. 2, 2024 (JP) ................................ 2024-014975

(51) Int. Cl.
*A61B 34/20* (2016.01)
*A61B 90/00* (2016.01)

(52) U.S. Cl.
CPC .............. *A61B 34/20* (2016.02); *A61B 90/37* (2016.02); *A61B 2034/2051* (2016.02);
(Continued)

(58) Field of Classification Search
CPC ...... A61B 2090/376; A61B 2090/3782; A61B 34/20; A61B 2034/2051;
(Continued)

(56) References Cited

U.S. PATENT DOCUMENTS

2012/0245458 A1 9/2012 Gogin et al.
2015/0223773 A1* 8/2015 John .................... A61B 8/0841 600/424
2021/0145412 A1 5/2021 Mansi et al.

FOREIGN PATENT DOCUMENTS

JP 2017-68468 A 4/2017

OTHER PUBLICATIONS

Extended European Search Report issued Apr. 16, 2024, in corresponding European Patent Application No. 24157910.1, 8 pages.

* cited by examiner

*Primary Examiner* — Chao Sheng
(74) *Attorney, Agent, or Firm* — Oblon, McClelland, Maier & Neustadt, L.L.P.

(57) ABSTRACT

An X-ray diagnostic apparatus according to an embodiment includes a processor. The processor sequentially acquires ultrasonic image data generated from a signal collected from a detector of an ultrasonic catheter that is inserted into a body of a subject. The processor collects a plurality of pieces of X-ray image data acquired from a plurality of directions and detects the ultrasonic catheter and a treatment device on the X-ray image data. The processor calculates coordinates indicating a current position of the treatment device on the X-ray image data based on information about a user operation for the ultrasonic catheter received from a robot catheter system, the treatment device detected on the ultrasonic image data, and a result of detection by the detector. The processor displays a display image that is obtained by superimposing positional information including the coordinates indicating the current position of the treatment device onto the X-ray image data.

16 Claims, 15 Drawing Sheets

(52) U.S. Cl.
CPC ................. *A61B 2034/2059* (2016.02); *A61B 2034/2065* (2016.02); *A61B 2090/364* (2016.02); *A61B 2090/376* (2016.02); *A61B 2090/3782* (2016.02); *A61B 2090/3966* (2016.02)

(58) Field of Classification Search
CPC .... A61B 2034/2059; A61B 2034/2065; A61B 90/37; A61B 2090/364; A61B 2090/3966
See application file for complete search history.

X-RAY DIAGNOSTIC APPARATUS, X-RAY DIAGNOSTIC SYSTEM, AND X-RAY DIAGNOSTIC METHOD

FIELD

This application is based upon and claims the benefit of priority from Japanese Patent Application No. 2023-021565, filed on Feb. 15, 2023; and Japanese Patent Application No. 2024-014975, filed on Feb. 2, 2024; the entire contents of which are incorporated herein by reference.

Embodiments disclosed in this specification and in the drawings are related to an X-ray diagnostic apparatus, an X-ray diagnostic system, and an X-ray diagnostic method.

BACKGROUND

Treatments for some structural heart diseases, such as a left atrial appendage occlusion, have been performed by using both an X-ray diagnostic apparatus (for example, X-ray angiography) and an intracardiac echocardiography (ICE).

At least two devices are inside the heart during manipulation, the devices including for example a catheter including an occlusion stent and an ICE catheter. Fluoroscopy is used in main to navigate each catheter to a target site or to place a treatment device (for example, stent, etc.). The ICE is always in use during the manipulation. It is desired to reduce the fluoroscopy time as much as possible to meet a need for reduction of operator's or patient's exposure to radiation.

DETAILED DESCRIPTION

An X-ray diagnostic apparatus according to an embodiment includes a processor. The processor sequentially acquires ultrasonic image data generated from a signal collected from a detector of an ultrasonic catheter that is inserted into a body of a subject. The processor collects a plurality of pieces of X-ray image data that are captured from a plurality of directions and detects the ultrasonic catheter and a treatment device on the X-ray image data. The processor calculates coordinates indicating a current position of the treatment device on the X-ray image data based on operation information about a user operation for the ultrasonic catheter received from a robot catheter system, the treatment device detected on the ultrasonic image data, and a result of detection by the detector. The operation information may be a numerical value. The processor displays a display image that is obtained by superimposing positional information including the coordinates indicating the current position of the treatment device onto the X-ray image data.

Embodiments of an X-ray diagnostic apparatus will be described in detail below with reference to the drawings. In the following explanation, if a component has the same or substantially the same function as an already-explained one with respect to an already-explained drawing, the same reference sign is assigned to that component, and its explanation may be repeated only when it is required. For ones representing the same part, they may be illustrated with different dimensions and ratios depending on drawings.

In addition, for purpose of good visibility for the drawings for example, in explanation for the respective drawings, the reference signs may be assigned to only main components and the reference sign may not be assigned even to a component having the same or substantially the same function.

Embodiments

Figure 1:
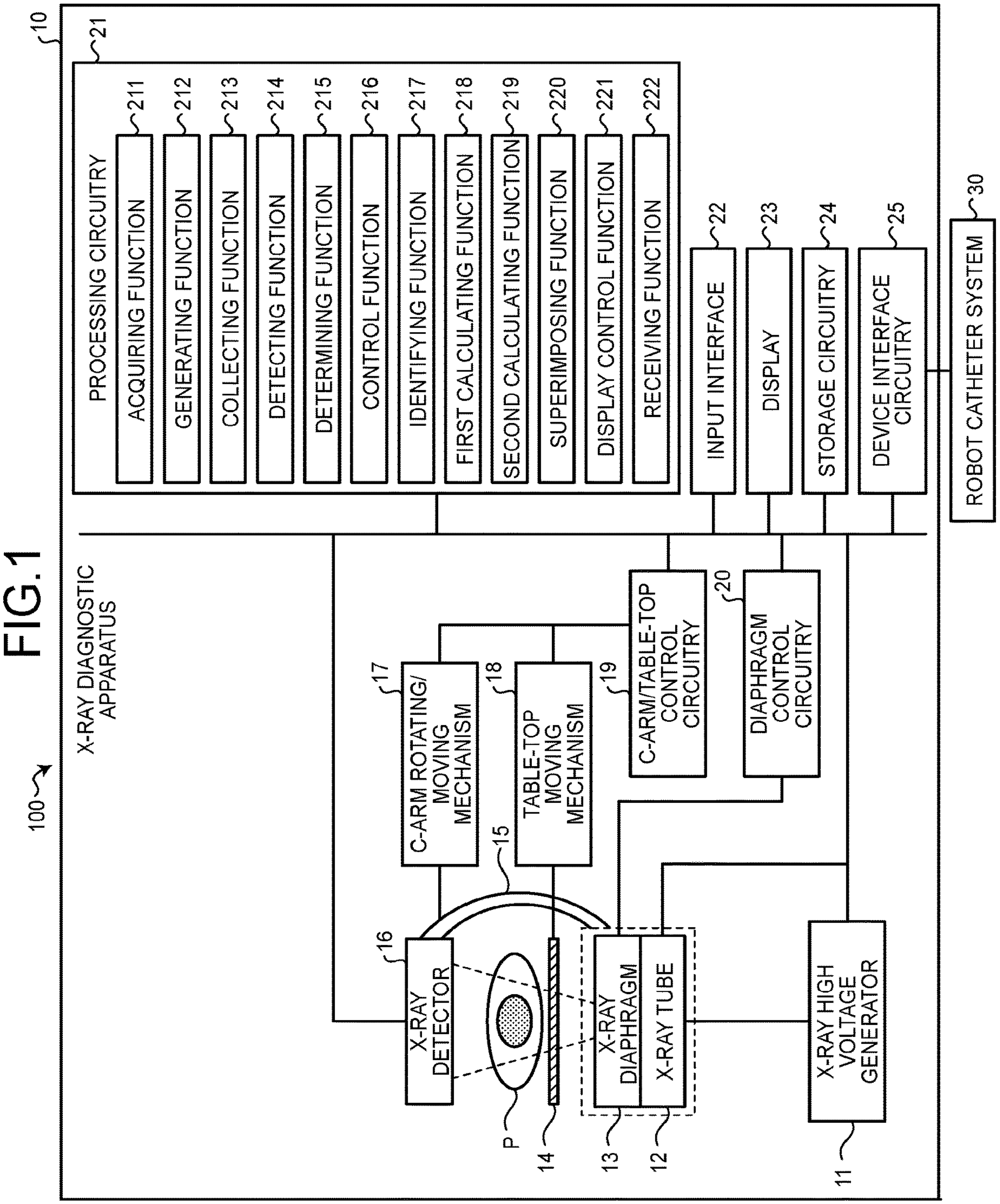
FIG. 1 is a block diagram illustrating an example of a configuration of an X-ray diagnostic apparatus according to an embodiment.

FIG. 1 is a block diagram illustrating an example of a configuration of an X-ray diagnostic system 100 according to a first embodiment. As illustrated in FIG. 1, the X-ray diagnostic system 100 includes an X-ray diagnostic apparatus 10 and a robot catheter system 30.

The robot catheter system 30 includes a remote catheter and a remote console. The remote catheter includes a robot arm, an intracardiac echocardiography (ICE) catheter, and an occlusion catheter. The remote catheter inserts, under control of the remote console, the ICE catheter and the occlusion catheter into a predetermined site (for example, an affected site) of a subject via the robot arm. The ICE catheter captures an image of inside of a cardiac cavity of the subject with a transducer included in the ICE catheter. The ICE catheter is an example of an ultrasonic catheter. The occlusion catheter is a device for blocking a predetermined site of a subject. The occlusion catheter is an example of a treatment device. The transducer is an example of a detector.

The robot catheter system 30 transmits an amount of feed in a direction along a shaft of the ICE catheter and an amount of rotation around the shaft to the X-ray diagnostic apparatus 10 together with timestamp information. An ultrasonic diagnostic apparatus (not illustrated) connected to the robot catheter system 30 generates ultrasonic image data based on a signal collected by the transducer and transmits the ultrasonic image data to the X-ray diagnostic apparatus 10. It is noted that the robot catheter system 30 may generate ultrasonic image data and transmit the generated ultrasonic image data to the X-ray diagnostic apparatus 10 together with timestamp information. The timestamp information includes information of an operation time when the robot catheter system 30 is operated.

The X-ray diagnostic apparatus 10 includes an X-ray high voltage generator 11, an X-ray tube 12, an X-ray diaphragm 13, a table-top 14, a C-arm 15, an X-ray detector 16, a C-arm rotating/moving mechanism 17, a table-top moving mechanism 18, C-arm/table-top control circuitry 19, diaphragm control circuitry 20, processing circuitry 21, an input interface 22, a display 23, storage circuitry 24, and device interface circuitry 25. The X-ray diagnostic apparatus 10 is an angiography apparatus, for example.

The X-ray high voltage generator 11 is a high voltage power supply that generates a high power voltage and supplies the generated high voltage to the X-ray tube 12 under control of the processing circuitry 21.

The X-ray tube 12 generates an X-ray by using the high voltage supplied from the X-ray high voltage generator 11. The X-ray diaphragm 13 narrows down, under control of the diaphragm control circuitry 20, the X-ray generated by the X-ray tube 12 so as to selectively illuminate a region of interest (ROI) of a subject P.

The table-top 14 is a bed on which the subject P lies, and it is disposed on a not-illustrated table. The not-illustrated table may be included in the X-ray diagnostic apparatus 10, or it may be external to the X-ray diagnostic apparatus 10. It is noted that if the table is not included in the X-ray diagnostic apparatus 10, the table may be included in the X-ray diagnostic system 100. It is noted that the subject P is not included in the X-ray diagnostic apparatus 10.

The X-ray detector 16 is an X-ray flat panel detector (FPD) having a plurality of detection elements arranged in a matrix shape. It is noted that the X-ray detector 16 may be an indirectly converting detector having a scintillator array and an optical sensor array or a directly converting detector having a semiconductor element that converts an incident X-ray into an electric signal.

As an example, each of the plurality of detection elements of the X-ray detector 16 has a complementary metal oxide semiconductor (CMOS) sensor and a scintillator. Each detection element generates a detection signal by, for example, converting a detected X-ray into an electric chart to accumulate the electric charge and then converting the accumulated electric charge into a voltage or current. The X-ray detector 16 outputs the detection signal to the processing circuitry 21.

The C-arm 15 holds the X-ray tube 12, the X-ray diaphragm 13, and the X-ray detector 16. The C-arm rotating/moving mechanism 17 is a mechanism for rotating and moving the C-arm 15 by driving a motor etc., provided on a supporter. The table-top moving mechanism 18 is a mechanism for moving the table-top 14. For example, the table-top moving mechanism 18 moves the table-top 14 with a power generated by an actuator.

The C-arm/table-top control circuitry 19 adjusts rotation and movement of the C-arm 15 and movement of the table-top 14 by controlling the C-arm rotating/moving mechanism 17 and the table-top moving mechanism 18 under control of the processing circuitry 21. The diaphragm control circuitry 20 controls a range of illumination where the X-ray illuminates the subject P by adjusting an aperture degree of an aperture blade included in the X-ray diaphragm 13 under control of the processing circuitry 21.

The input interface 22 is implemented by a trackball, a switch button, a mouse, a keyboard, a touchpad with which an input operation is made through a touch on an operation screen, a touchscreen that is a unification of a display screen and a touchpad, contactless input circuitry and audio input circuitry using an optical sensor, etc. The input interface 22 is connected to the processing circuitry 21, and the input interface 22 converts an input operation received from a user into an electric signal and outputs the electric signal to the processing circuitry 21.

It is noted that the input interface 22 is not limited to ones having physical operation parts, such as a mouse and a keyboard. Examples of the input interface 22 include electric-signal processing circuitry that receives an electric signal corresponding to an input operation from an external input device that is provided separately from the apparatus and outputs the electric signal to the processing circuitry 21, for example.

The display 23 is a liquid crystal display (LCD), an organic electro luminescence display (OELD), or the like, and it displays various types of information. The display 23 displays, for example, a graphical user interface (GUI) that is used to receive various instructions, settings, etc., from a user via the input interface 22.

The display 23 further displays various images generated by the processing circuitry 21. The display 23 is an example of a display unit. It is noted that the input interface 22 and the display 23 may form a touch panel.

The device interface circuitry 25 acquires an amount of feed in a direction along the shaft of the ICE catheter and an amount of rotation around the shaft, those transmitted by the robot catheter system 30, and stores in the storage circuitry 24 the acquired amount of feed in the direction along the shaft of the ICE catheter and the acquired amount of rotation around the shaft. The device interface circuitry 25 acquires ultrasonic image data that is transmitted by the ultrasonic diagnostic apparatus connected to the robot catheter system 30 and stores the acquired ultrasonic image data in the storage circuitry 24. The device interface circuitry 25 may store a time when an amount of feed in the direction along the shaft of the ICE catheter and an amount of rotation around the shaft are acquired in association with the amount of feed in the direction along the shaft of the ICE catheter and the amount of rotation around the shaft.

The storage circuitry 24 is implemented, for example, by a semiconductor memory element such as a random access memory (RAM) or a flash memory, a hard disk, an optical disc, etc. For example, the storage circuitry 24 stores therein a program performed by any circuitry included in the X-ray diagnostic apparatus 10.

The processing circuitry 21 is a processor that reads a program from the storage circuitry 24 and executes the program to implement a function corresponding to the program. The processing circuitry 21 according to the present embodiment includes an acquiring function 211, a generating function 212, a collecting function 213, a detecting function 214, a determining function 215, a control function 216, an identifying function 217, a first calculating function 218, a second calculating function 219, a superimposing function 220, a display control function 221, and a receiving function 222.

The acquiring function 211 is an example of an acquiring unit. The generating function 212 is an example of a generating unit. The collecting function 213 is an example of a collecting unit. The detecting function 214 is an example of a detecting unit. The determining function 215 is an example of a determining unit. The control function 216 is an example of a control unit. The identifying function 217 is an example of an identifying unit. The first calculating function 218 is an example of a first calculating unit. The second calculating function 219 is an example of a second calculating unit. The superimposing function 220 is an example of a superimposing unit. The display control function 221 is an example of a display control unit. The receiving function 222 is an example of a receiving unit.

Herein, for example, the respective processing functions, which are components of the processing circuitry 21, are stored in the storage circuitry 24 in form of a program executable by a computer, the respective processing functions including: the acquiring function 211, the collecting function 213, the detecting function 214, the determining function 215, the control function 216, the identifying function 217, the first calculating function 218, the second calculating function 219, the superimposing function 220, the display control function 221, and the receiving function 222. The processing circuitry 21 is a processor.

For example, the processing circuitry 21 reads a program from the storage circuitry 24 and executes the program to implement a function corresponding to the program. In other words, when the processing circuitry 21 reads the respective programs, the processing circuitry 21 has the respective functions illustrated in the processing circuitry 21 of FIG. 1.

It has been explained with respect to FIG. 1 that a single processor implements the processing functions performed by the collecting function 213, the detecting function 214, the determining function 215, the control function 216, the identifying function 217, the first calculating function 218, the second calculating function 219, the superimposing function 220, the display control function 221, and the receiving function 222; however, it is allowable to form the processing circuitry 21 by combining two or more independent processors and to implement the functions by the respective processors performing the programs.

Moreover, it has been explained with respect to FIG. 1 that the single storage circuitry 24 stores the programs corresponding to the respective processing functions; however, it is allowable to provide two or more storage circuits dispersedly and design the processing circuitry 21 to read a corresponding program from an individual storage circuit.

An example has been described above where the "processor" reads a program corresponding to each function and executes the program; however, embodiments are not limited to this. The term "processor" means circuitry, such as a central processing unit (CPU), a graphics processing unit (GPU), an application specific integrated circuit (ASIC), a programmable logic device (for example, a simple programmable logic device (SPLD), a complex programmable logic device (CPLD), and a field programmable gate array (FPGA)), for example.

If the processor is a CPU for example, the processor implements a function by reading a program stored in the storage circuitry and executing the program. If, in contrast, the processor is an ASIC, the function is directly incorporated into circuitry of the processor as logic circuitry, instead of storing the program in the storage circuitry 24.

It is noted that the processors of the present embodiment are not limited to a single circuit for each processor, and it is allowable to form a single processor by combining two or more independent circuits and implement its function. Furthermore, it is allowable to integrate two or more components illustrated in FIG. 1 into one processor and implement their functions.

The acquiring function 211 acquires, via the device interface circuitry 25, ICE catheter's operation information transmitted by the robot catheter system 30. The ICE catheter's operation information includes, for example, at least one of an amount of feed in the direction along the shaft of the ICE catheter or an amount of rotation around the shaft. Moreover, the acquiring function 211 sequentially acquires, via the device interface circuitry 25, ultrasonic image data transmitted by the ultrasonic diagnostic apparatus, the ultrasonic image data being generated from a signal collected by the transducer that is inserted into the body of the subject. The acquiring function 211 stores in the storage circuitry 24 the acquired amount of feed in the direction along the shaft of the ICE catheter and amount of rotation around the shaft and the ultrasonic image data.

The generating function 212 generates X-ray image data from a detection signal detected by the X-ray detector 16 and stores the generated X-ray image data in the storage circuitry 24. For example, the generating function 212 generates X-ray image data by performing current/voltage conversion, A/D conversion, and parallel/serial conversion on the detection signal detected by the X-ray detector 16.

Moreover, the generating function 212 may perform image processing, such as noise reduction processing, on the X-ray image data. The X-ray image data of the present embodiment is explained as fluoroscopic image data; however, the present embodiment is applicable to a digital angiography (DA) image, etc., in the same manner.

Figure 2:
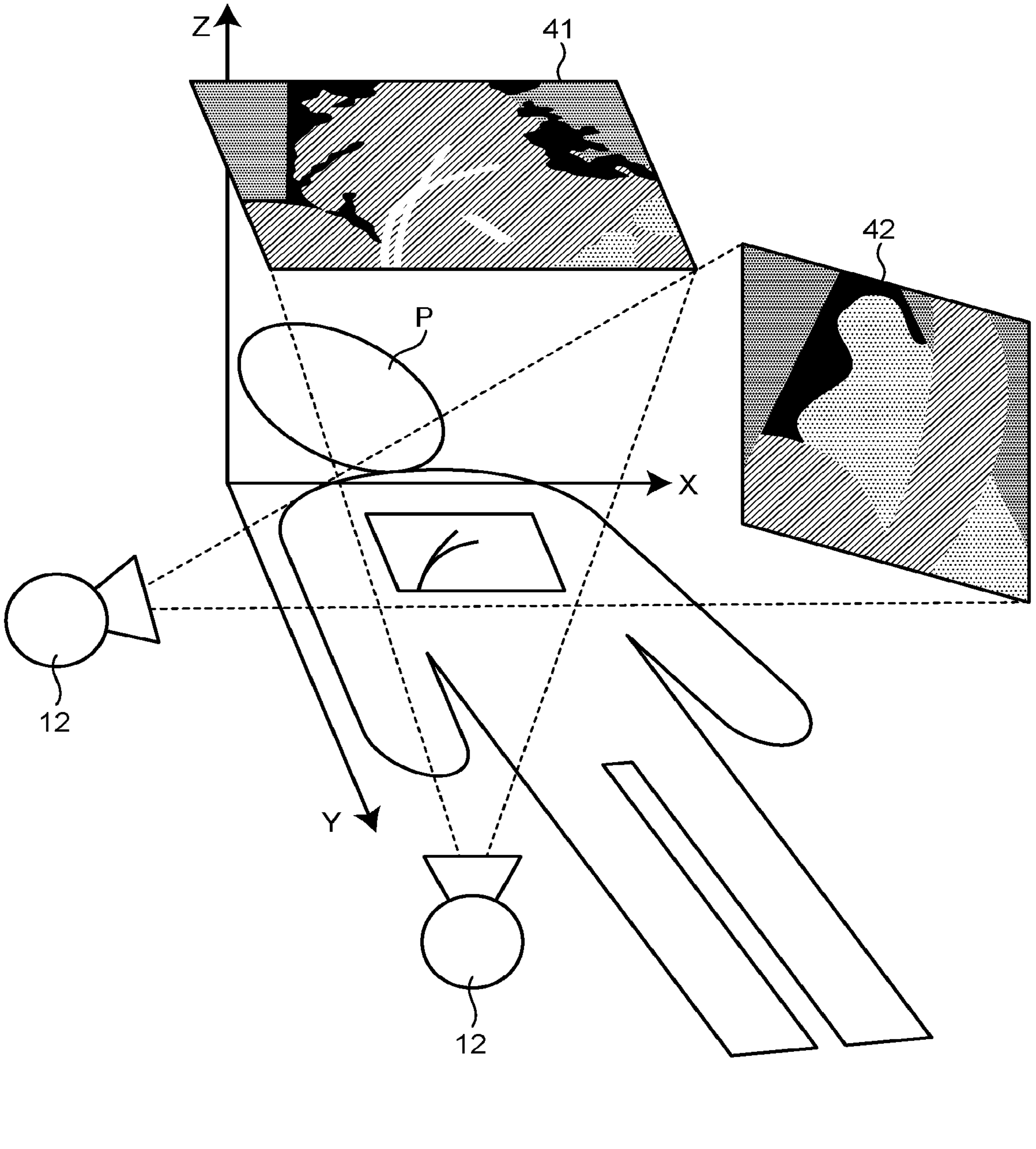
FIG. 2 is a schematic diagram illustrating an example of X-ray image data according to the embodiment.

The collecting function 213 collects X-ray image data. More particularly, the collecting function 213 collects X-ray image data generated by the generating function 212. Explained below using FIG. 2 is X-ray image data collected by the collecting function 213. FIG. 2 is a schematic diagram illustrating an example of X-ray image data according to the embodiment.

The collecting function 213 collects a plurality of pieces of X-ray image data generated by the generating function 212. FIG. 2 illustrates X-ray image data 41 and X-ray image data 42. The X-ray image data 41 is a piece of X-ray image data generated by the generating function 212, the X-ray image data 41 being obtained by capturing an image of the subject P with the X-ray tube 12 pointing in a Z-axis direction. The X-ray image data 42 is a piece of X-ray image data generated by the generating function 212, the X-ray image data 42 being obtained by capturing an image of the subject P with the X-ray tube 12 pointing in an X-axis direction.

Returning back to FIG. 1. The detecting function 214 detects an object on X-ray image data. More particularly, the detecting function 214 detects an object drawn on X-ray image data collected by the collecting function 213. The object drawn on X-ray image data is, for example, a device such as the ICE catheter or the occlusion catheter. More particularly, the detecting function 214 detects any device drawn in each of a plurality of frames included in the X-ray image data on one-frame basis. Such a device is inserted into a blood vessel of the subject P through manipulation by a doctor.

Figure 3:
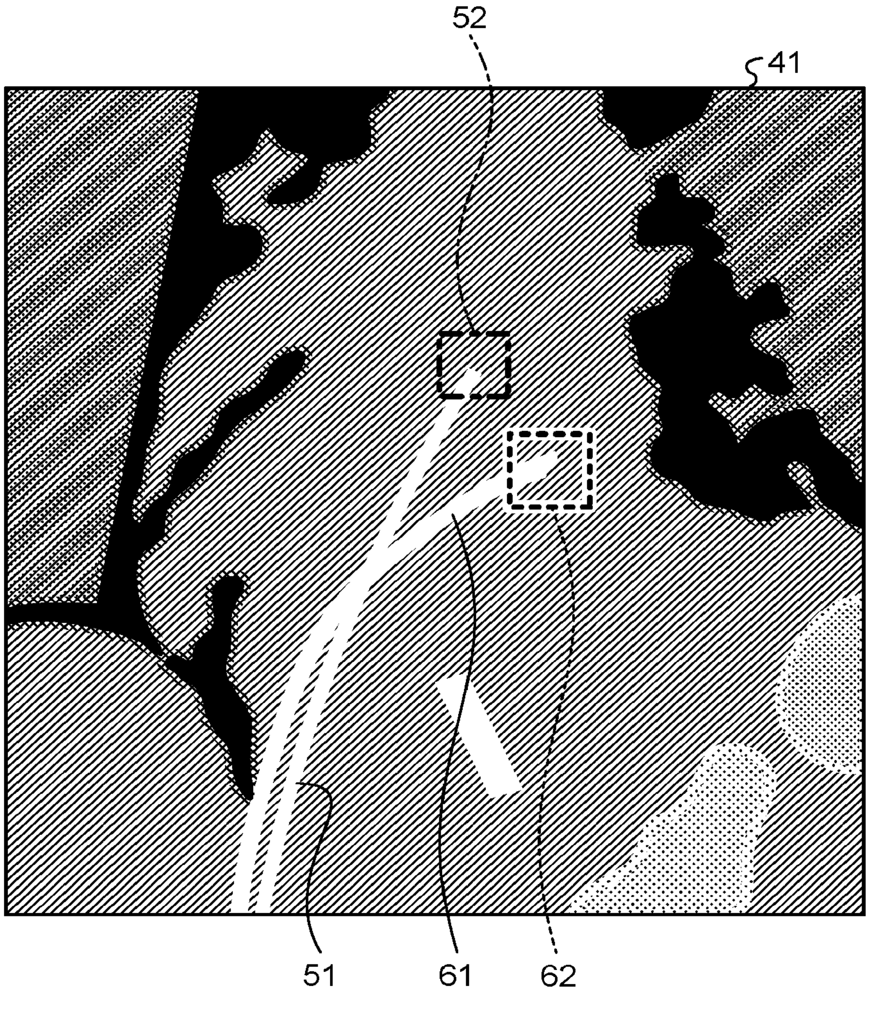
FIG. 3 is a schematic diagram illustrating an example of an object detected in the X-ray image data according to the embodiment.

Explained herein, using FIG. 3, is an object detected by the detecting function 214. FIG. 3 is a schematic diagram illustrating an example of the object detected in the X-ray image data according to the embodiment. The X-ray image data 41 as illustrated in FIG. 3 indicates an ICE catheter 51 and an occlusion catheter 61. The detecting function 214 detects the ICE catheter 51 and the occlusion catheter 61 drawn in the X-ray image data 41. Moreover, the detecting function 214 detects the transducer (detector) for the ICE catheter drawn in the X-ray image data 41.

Furthermore, the detecting function 214 detects an opaque marker that is present at a leading end of the occlusion catheter from ultrasonic image data generated by the robot catheter system 30. More particularly, the detecting function 214 detects an opaque marker that is present at the leading end of the occlusion catheter from ultrasonic image data acquired by the acquiring function 211.

Returning back to FIG. 1. The determining function 215 determines whether the occlusion catheter is detected in the ultrasonic image data. More particularly, the determining function 215 determines whether the detecting function 214 detects the opaque marker, which is present at the leading end of the occlusion catheter, included in the object drawn in the ultrasonic image data.

When no occlusion catheter is detected from the ultrasonic image data, the control function 216 performs, based on the operation information, at least one of a notification concerning second X-ray illumination or a control for the second X-ray illumination. For example, when the determining function 215 determines that no occlusion catheter is detected in the ultrasonic image data, the control function 216 performs at least one of a notification concerning second X-ray illumination or a control for the second X-ray illumination based on the operation information acquired by the acquiring function 211.

The identifying function 217 identifies an initial position of the ICE catheter. More particularly, the identifying function 217 identifies an initial position of the ICE catheter detected by the detecting function 214. For example, when the ICE catheter and the occlusion catheter are inside a cardiac cavity simultaneously, the identifying function 217 identifies an initial position of the ICE catheter that is detected when X-rays illuminate from a plurality of directions by fluoroscopy or one-shot. FIG. 3 illustrates an initial position 52 of the ICE catheter identified by the identifying function 217.

Moreover, the identifying function 217 identifies an initial position of the occlusion catheter. More particularly, the identifying function 217 identifies an initial position of the occlusion catheter detected by the detecting function 214. For example, when the ICE catheter and the occlusion catheter are inside a cardiac cavity simultaneously, the identifying function 217 identifies an initial position of the occlusion catheter that is detected when X-rays illuminate from a plurality of directions by fluoroscopy or one-shot imaging. FIG. 3 illustrates an initial position 62 of the occlusion catheter identified by the identifying function 217.

The first calculating function 218 calculates coordinates indicating the initial leading-end position of the ICE catheter from the transducer (detector) of the ICE catheter. More particularly, the first calculating function 218 calculates coordinates indicating the initial leading-end position of the ICE catheter based on a barycenter and a plurality of directional vectors of the transducer (detector) of the ICE detected by the detecting function 214. The plurality of directional vectors includes, for example, a first directional vector, a second directional vector, and a third directional vector.

Figure 4:
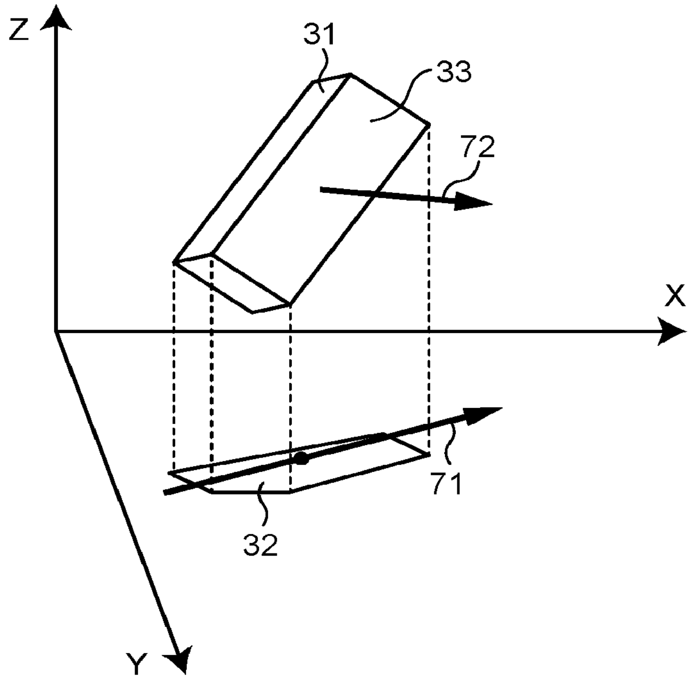
FIG. 4 is a schematic diagram illustrating an example of directional vectors according to the embodiment.
Figure 5:
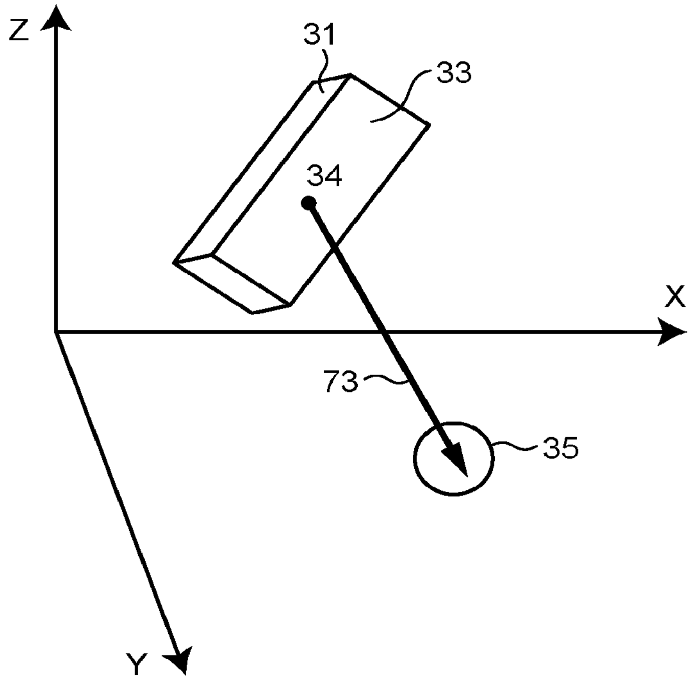
FIG. 5 is a schematic diagram illustrating an example of directional vectors according to the embodiment.

The plurality of directional vectors are explained herein by using FIGS. 4 and 5. FIGS. 4 and 5 are schematic diagrams each illustrating an example of directional vectors according to the embodiment. FIGS. 4 and 5 illustrate a transducer 31 of the ICE catheter.

A first directional vector 71 is a directional vector obtained when the transducer 31 of the ICE catheter is projected onto a plane (an XY plane in FIG. 4) parallel to a transducer 32 on the X-ray image data. A second directional vector 72 is a directional vector (normal vector) perpendicular to a surface 33 of the transducer 31 of the ICE catheter. A third directional vector 73 is a relative-position vector for an occlusion-catheter leading-end position 35 when viewed from an ICE-catheter barycentric position 34. The plurality of directional vectors are calculated by, for example, principles of stereoscopic vision (trigonometry), etc.

Moreover, the first calculating function 218 calculates coordinates indicating a current position of the ICE catheter on the X-ray image data. More particularly, the first calculating function 218 calculates coordinates indicating a current position of the ICE catheter on the X-ray image data based on the amount of feed in the direction along the shaft of the ICE catheter included in the ICE catheter's operation information acquired by the acquiring function 211, the first directional vector included in the plurality of directional vectors, and the coordinates indicating the initial leading-end position of the ICE catheter.

The second calculating function 219 calculates coordinates indicating a current position of the occlusion catheter on the X-ray image data. More particularly, the second calculating function 219 calculates coordinates indicating a current position of the occlusion catheter on the X-ray image data based on an amount of change, with respect to the second directional vector, in the amount of rotation around the shaft of the ICE catheter included in the ICE catheter's operation information acquired by the acquiring function 211, the third directional vector, and the opaque marker.

Returning back to FIG. 1. The superimposing function 220 superimposes, on the X-ray image data, positional information including the coordinates indicating the current position of the ICE catheter and the coordinates indicating the current position of the occlusion catheter. More particularly, the superimposing function 220 superimposes, on the X-ray image data generated by the generating function 212, positional information including the coordinates indicating the current position of the ICE catheter calculated by the first calculating function 218 and the coordinates indicating the current position of the occlusion catheter calculated by the second calculating function 219.

Figure 6:
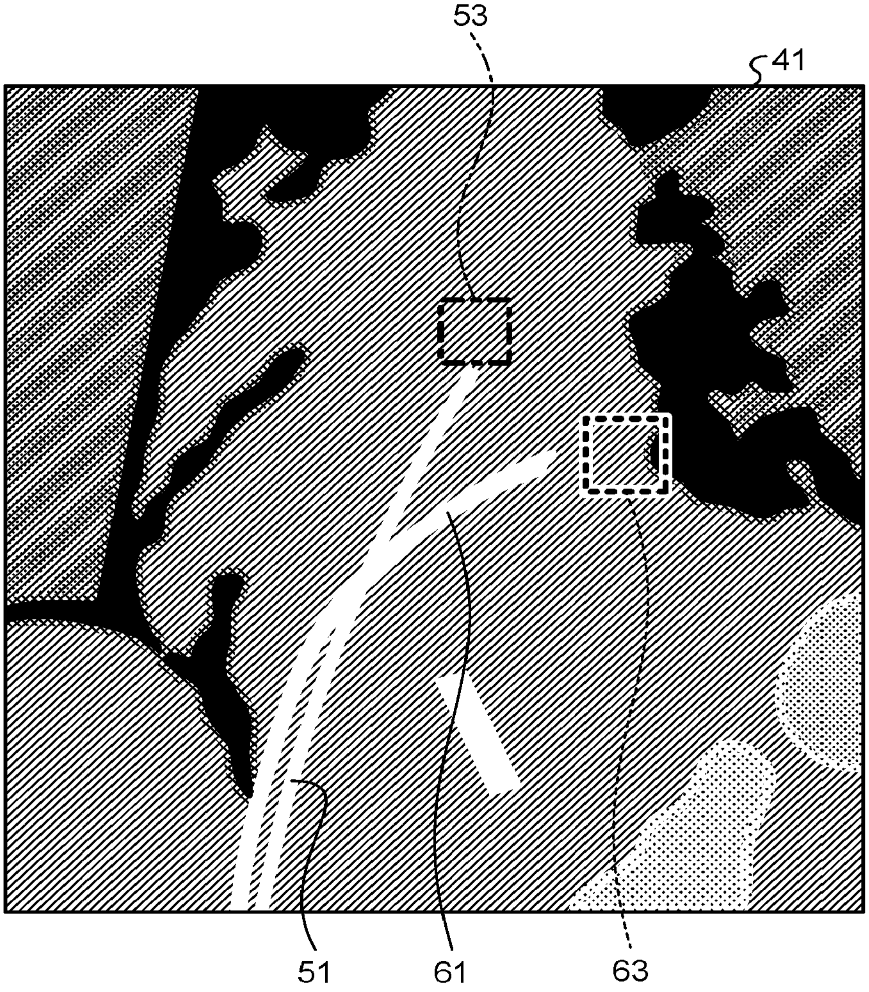
FIG. 6 is a schematic diagram illustrating an example of X-ray image data on which positional information on the object is superimposed according to the embodiment.

The X-ray image data on which the superimposing function 220 superimposes the positional information is explained herein by using FIG. 6. FIG. 6 is a schematic diagram illustrating an example of the X-ray image data on which the positional information is superimposed according to the embodiment. FIG. 6 is, for example, a schematic diagram illustrating an example of X-ray image data that is obtained by superimposing the coordinates indicating the current position of the object on the X-ray image data 41 as illustrated in FIG. 3.

FIG. 6 illustrates positional information including coordinates (current position) 53 indicating the current position of the ICE catheter and coordinates (current position) 63 indicating the current position of the occlusion catheter. When the coordinates 53 indicating the current position of the ICE catheter as illustrated in FIG. 6 are compared to the initial position 52 of the ICE catheter as illustrated in FIG. 3, it is found that the current position of the ICE catheter indicated by the coordinates 53 changes from the initial position 52 of the ICE catheter.

Moreover, when the coordinates (current position) 63 indicating the current position of the occlusion catheter as illustrated FIG. 6 are compared to the initial position 62 of the occlusion catheter as illustrated in FIG. 3, it is found that the current position of the occlusion catheter indicated by the coordinates 63 changes from the initial position 62 of the occlusion catheter.

Thus, by calculating the positional information including the coordinates (current position) 53 indicating the current position of the ICE catheter and the coordinates (current position) 63 indicating the current position of the occlusion catheter, the X-ray diagnostic apparatus 10 enables the operator to see the ICE catheter and the occlusion catheter even when imaging by the X-ray diagnostic apparatus 10 is less performed. This enables a manipulation with a lower amount of X-ray used than the conventional technologies.

Returning back to FIG. 1. The display control function 221 displays a graphical user interface (GUI) and an X-ray image on the display 23. For example, the display control function 221 reads X-ray image data from the storage circuitry 24 in accordance with a user operation via the input interface 22 and outputs the X-ray image data on the display 23. Moreover, for example, the display control function 221 outputs to (displays on) the display 23 a display image that is obtained by superimposing the positional information including the coordinates indicating the current position of the treatment device on the X-ray image data. Furthermore, for example, the display control function 221 displays positions corresponding to the coordinates indicating the respective current positions including the occlusion catheter and the ICE catheter in a distinguishable manner. For example, the display control function 221 may mark (emphasize) and display positions corresponding to the coordinates indicating the respective current positions including the occlusion catheter and the ICE catheter. Moreover, for example, when acquiring latest X-ray image data, the display control function 221 may display a display image based on the latest X-ray image data.

The receiving function 222 receives a user's operation via the input interface 22. For example, the receiving function 222 receives a user's operation to select an imaging mode. Moreover, the receiving function 222 receives a user's operation to instruct a start of imaging and a user's operation to instruct an end of imaging.

Figure 7:
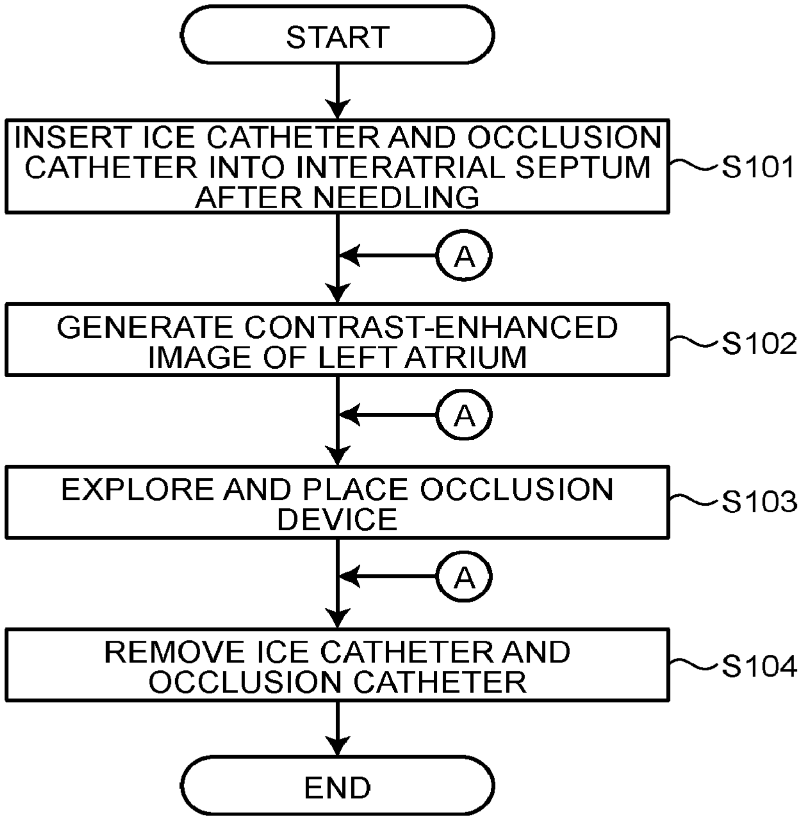
FIG. 7 is a flowchart illustrating an example of processing performed by a robot catheter system according to the embodiment.

Explained below is a flow of processing (manipulation) performed by the robot catheter system 30 according to the present embodiment. FIG. 7 is a flowchart illustrating an example of processing performed by the robot catheter system 30 according to the embodiment.

Firstly, the robot catheter system 30 inserts the ICE catheter and the occlusion catheter into the interatrial septum of the subject P after needling (Step S101). The robot catheter system 30 then injects a contrast agent into the left atrium of the subject P and generates contrast-enhanced X-ray image data (Step S102). The robot catheter system 30 then explores the occlusion device for the left atrium of the subject P and places it in a blood vessel (Step S103).

Subsequently, the robot catheter system 30 removes the ICE catheter and the occlusion catheter from the subject P (Step S104). The end of Step S104 leads to the end of the present processing. Processing A of the X-ray diagnostic apparatus 10 is performed during each interval between Step S101 and Step S102, between Step S102 and Step S103, and between Step S103 and Step S104.

Figure 8:
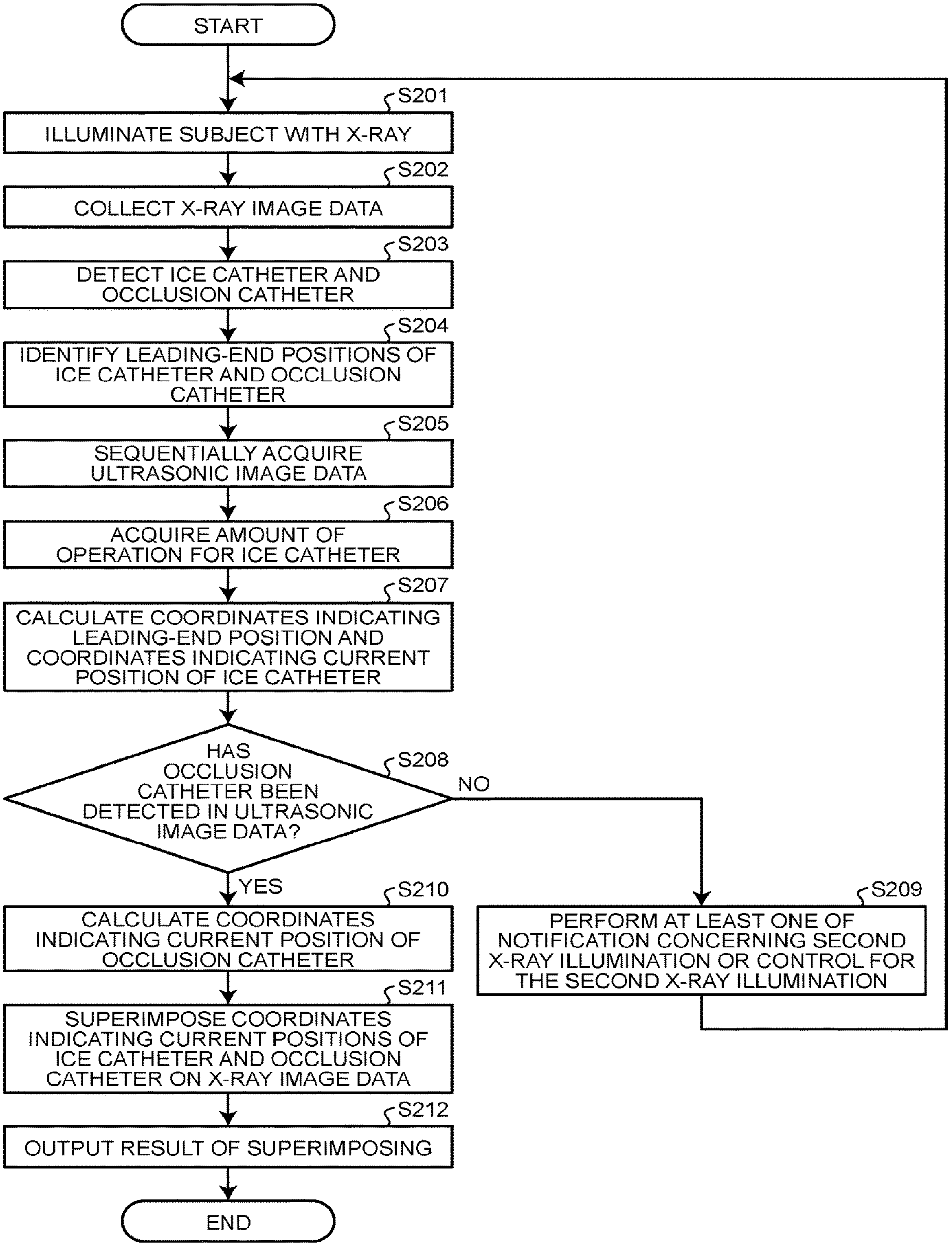
FIG. 8 is a flowchart illustrating an example of processing performed by an X-ray diagnostic apparatus according to the embodiment.

Explained subsequently is a flow of the processing A performed by the X-ray diagnostic apparatus 10 according to the present embodiment. FIG. 8 is a flowchart illustrating an example of processing performed by the X-ray diagnostic apparatus 10 according to the embodiment.

Firstly, the X-ray tube 12 illuminates the subject P with an X-ray (Step S201). The collecting function 213 then collects X-ray image data (Step S202). The detecting function 214 then detects the ICE catheter and the occlusion catheter on the X-ray image data collected by the collecting function 213 (Step S203). The identifying function 217 then identifies initial leading-end positions of the ICE catheter and the occlusion catheter (Step S204).

Subsequently, the acquiring function 211 sequentially acquires ultrasonic image data transmitted by the ultrasonic diagnostic apparatus (Step S205). The acquiring function 211 then acquires an amount of feed in a direction along the shaft of the ICE catheter and an amount of rotation around the shaft (Step S206). The first calculating function 218 then calculates coordinates indicating a leading-end position and coordinates indicating a current leading-end position of the ICE catheter from the amount of operation for the ICE catheter (Step S207).

The determining function 215 determines whether the occlusion catheter has been detected in the ultrasonic image data (Step S208). When the determining function 215 determines that the occlusion catheter has not been detected in the ultrasonic image data (Step S208: No), the process proceeds to Step S209. On the other hand, when the determining function 215 determines that the occlusion catheter has been detected in the ultrasonic image data (Step S208: Yes), the process proceeds to Step S210.

At Step S209, when the occlusion catheter has not been detected in the ultrasonic image data, the control function 216 performs at least one of a notification concerning second X-ray illumination or a control for the second X-ray illumination (Step S209).

At Step S210, the identifying function 217 identifies the current leading-end position of the occlusion catheter. The second calculating function 219 then calculates coordinates indicating the current position of the occlusion catheter (Step S210). The superimposing function 220 then superimposes the positions of the ICE catheter and the occlusion catheter on the X-ray image data (Step S211). The display control function 221 then outputs the X-ray image data on which the positional information is superimposed by the superimposing function 220 to the display 23 (Step S212). An end of Step S212 leads to an end of the present processing.

As described above, the X-ray diagnostic system 100 according to the present embodiment acquires ICE catheter's operation information, calculates coordinates indicating the current position of the ICE catheter on X-ray image data, and calculates coordinates indicating the current position of the treatment device on the X-ray image data based on the treatment device detected in ultrasonic image data and the operation information. After that, the X-ray diagnostic system 100 superimposes the coordinates indicating the current position of the ICE catheter and the coordinates indicating the current position of the treatment device on the X-ray image data and outputs the X-ray image data.

At least one of the embodiments as explained above can reduce fluoroscopy time for X-ray diagnosis with, for example, a manipulation in which a robot catheter system and an ICE cooperate together. This can reduce operator's or subject's exposure to X-ray radiation. Accordingly, the operator can perform a manipulation with a less amount of X-ray used than the conventional technologies. Moreover, by performing a manipulation with a less amount of X-ray used, contribution can be made to usage of robot catheter systems, whose market is expected to extend in the future.

Figure 9:
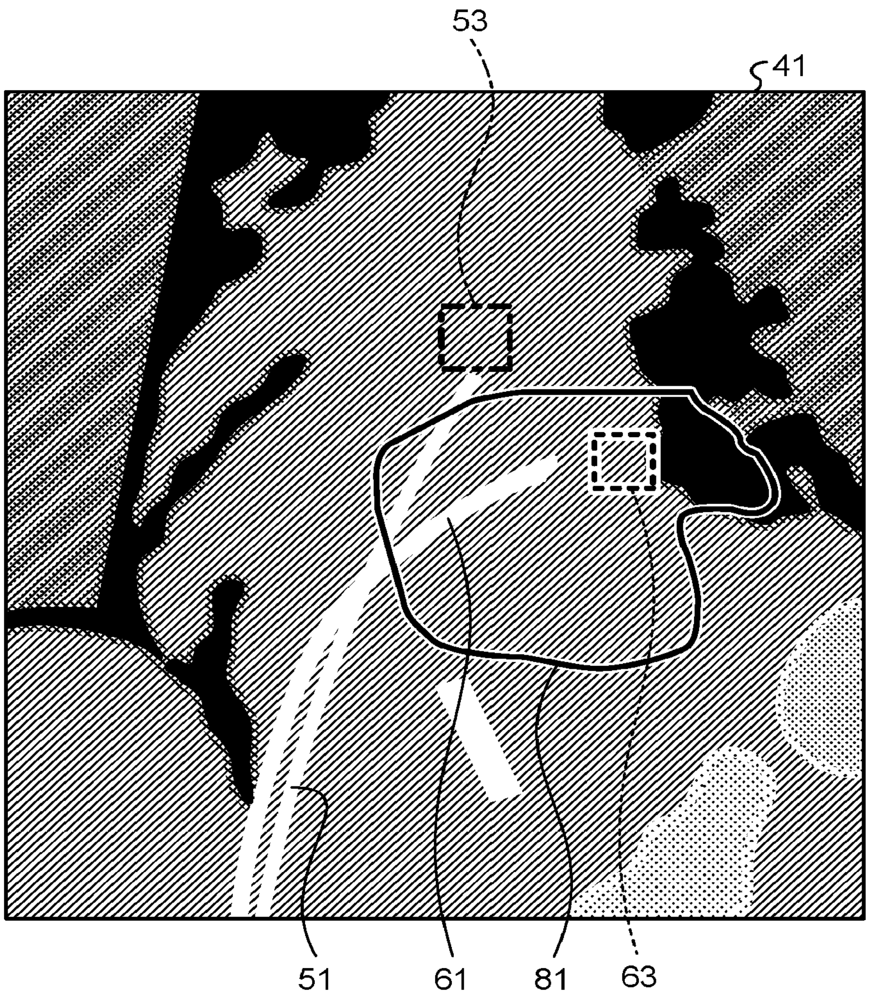
FIG. 9 is a schematic diagram illustrating an example of X-ray image data on which positional information on the object is superimposed according to a modification.
Figure 10:
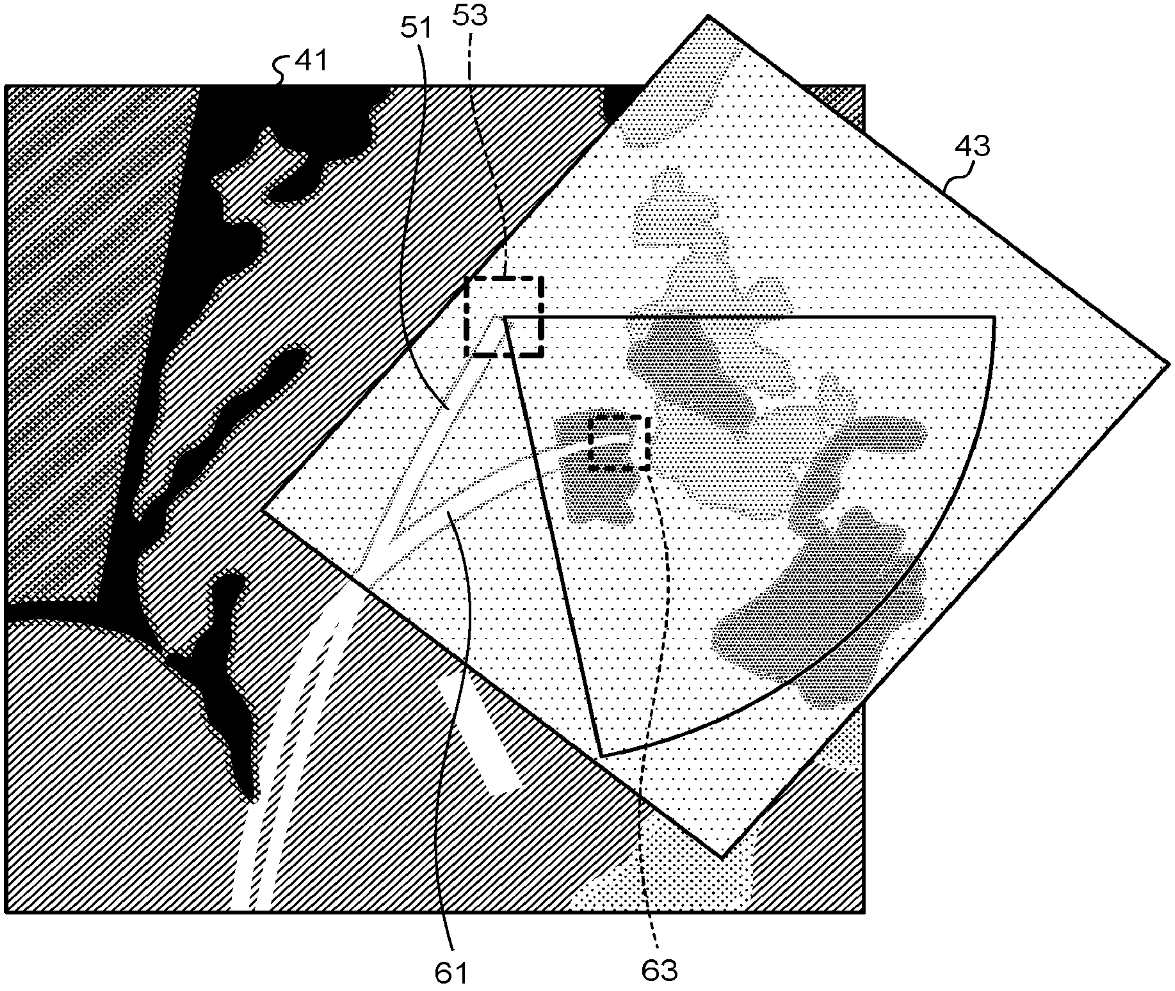
FIG. 10 is a schematic diagram illustrating an example of X-ray image data on which positional information is superimposed according to the modification.

Moreover, for example, because robot operations are less intuitive than direct catheter operations by the operator, an X-ray illumination time tends to increase to grasp the current position of the operation target. This results in unnecessary exposure to radiation. The present invention makes it possible to grasp the current position of the operation target without X-ray illumination, which allows a reduction of unnecessary exposure to radiation occurring in the robot operation First Modification An example has been explained in the above-mentioned embodiment in which the X-ray diagnostic apparatus 10 superimposes the positions of the objects (the ICE catheter and the occlusion catheter) on the X-ray image data. It is allowable, however, to superimpose something other than the objects on the X-ray image data. For example, the X-ray diagnostic apparatus 10 may superimpose, on the X-ray image data, collected image data information about a target to be treated. The image data information about a target to be treated is, for example, ultrasonic image data, information that is obtained by changing transparency of an ultrasonic image, information including a contour of the target to be treated, etc. FIGS. 9 and 10 are schematic diagrams each illustrating an example of X-ray image data on which positional information is superimposed according to a modification.

When, for example, an operator places a stent (occlusion catheter) in the left atrial appendage of the subject P, he/she confirms a positional relation between the stent and the left atrial appendage. For example, at Step S102 as illustrated in FIG. 7, for contrast-enhanced X-ray image data that is obtained through X-ray imaging with a contrast agent, the detecting function 214 of the processing circuitry 21 included in the X-ray diagnostic apparatus 10 detects a contour from the left atrium to the left atrial appendage.

The superimposing function 220 then may superimpose, on the X-ray image data 41 as illustrated in FIG. 9, a contour 81 from the left atrium to the left atrial appendage as well as the current position 53 of the ICE catheter 51 and the current position 63 of the occlusion catheter 61; and the display control function 221 may output the X-ray image data on which the contour 81 is superimposed.

Moreover, for example, the identifying function 217 may identify, from another X-ray image data, a view with which the left atrial appendage and the stent are recognizable; the superimposing function 220 may superimpose on the X-ray image data 41 as illustrated in FIG. 10 ultrasonic image data 43 generated by the robot catheter system 30 as well as the current position 53 of the ICE catheter 51 and the current position 63 of the occlusion catheter 61; and the display control function 221 may output the X-ray image data on which the ultrasonic image data 43 is superimposed. This enables the operator to confirm the positional relation between the stent and the left atrial appendage.

Second Modification

An example has been explained in the above-mentioned embodiment in which the acquiring function 211 included in the X-ray diagnostic apparatus 10 acquires an amount of feed in the direction along the shaft of the ICE catheter and an amount of rotation around the shaft, those transmitted by the robot catheter system 30. They correspond to a forward/backward movement in the direction along the shaft of the ICE catheter and an amount of rotation around the shaft of the transducer including the ICE catheter, respectively. Information that the acquiring function 211 acquires is not limited thereto.

When, for example, the leading end of the ICE catheter bends forward, backward, left, right, or the like, it is allowable to acquire a length and an angle of the bend from the robot catheter system 30. It is also allowable, for example, to recognize a situation where the ICE catheter bends and output second imaging or the like because there is a possibility that the position of the ICE catheter is incorrect. More particularly, the X-ray diagnostic apparatus 10 can detect a collision of the leading end of the ICE catheter or the occlusion catheter against a cardiac muscle or valve because anything other than the cardiac cavity appears white in ultrasonic image data.

Therefore, when an apparent difference is found between a distance between the ICE catheter and the occlusion catheter displayed on the X-ray image data captured by the X-ray tube 12 and a distance between the ICE catheter and the occlusion catheter on the ultrasonic image data generated by the robot catheter system 30, the X-ray diagnostic apparatus 10 recognizes there is a possibility that the position of the ICE catheter is incorrect.

With this configuration, the X-ray diagnostic apparatus 10 can recognize a situation where the ICE catheter bends and output second imaging, etc., because there is a possibility that the position of the ICE catheter is incorrect. It is noted that when the X-ray diagnostic apparatus 10 performs second imaging, the above-explained processing A is performed.

Third Modification

In the above-mentioned embodiment, as illustrated in FIG. 6, each of the current position 53 of the ICE catheter and the current position 63 of the occlusion catheter are displayed in the same color. When, for example, there is a possibility that a leading end of a catheter collides against a cardiac muscle or valve on the ultrasonic image data generated by the robot catheter system 30, it is allowable to display it in a different color to encourage awareness of the risk of collision. Anything other than the cardiac cavity appears white in ultrasonic image data; therefore, whether a leading end of a catheter may collide against a cardiac muscle or valve on the ultrasonic image data may be determined on the level of image, for example.

Fourth Modification

In the above-mentioned embodiment, the first directional vector 71 and the second directional vector 72 may be determined by detecting an opaque marker provided at the transducer of the ICE or at the leading end of the occlusion catheter; alternatively, the first directional vector 71 and the second directional vector 72 may be determined to smoothly link to not only the leading end of the occlusion catheter but also a curve line of the entire of the ICE catheter and the occlusion catheter.

Moreover, in the above-mentioned embodiment, the third directional vector may be determined from the X-ray image data 41 on which the initial position 52 of the ICE catheter and the initial position 62 of the occlusion catheter are superimposed as illustrated in FIG. 3. Alternatively, it is allowable to detect the occlusion catheter from the X-ray image data 41 and determine a relative-position vector for the ICE catheter viewed from the occlusion catheter.

Fifth Modification

Figure 11:
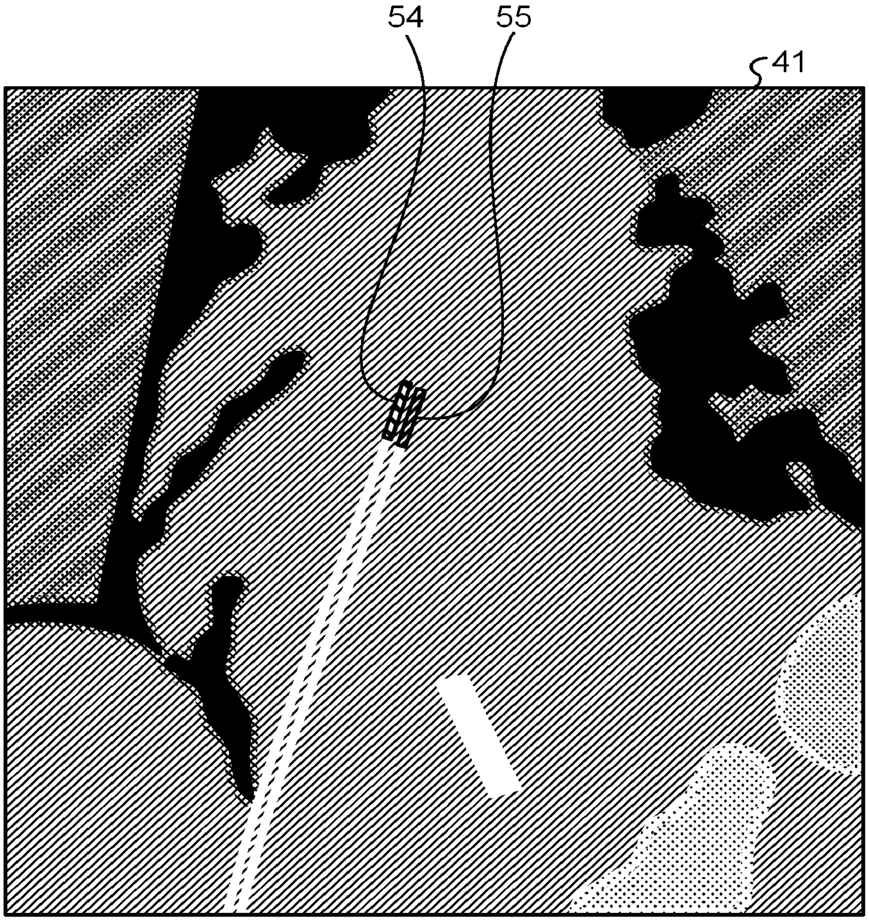
FIG. 11 is a schematic diagram illustrating an example of an object detected on the X-ray image data according to a modification.
Figure 12:
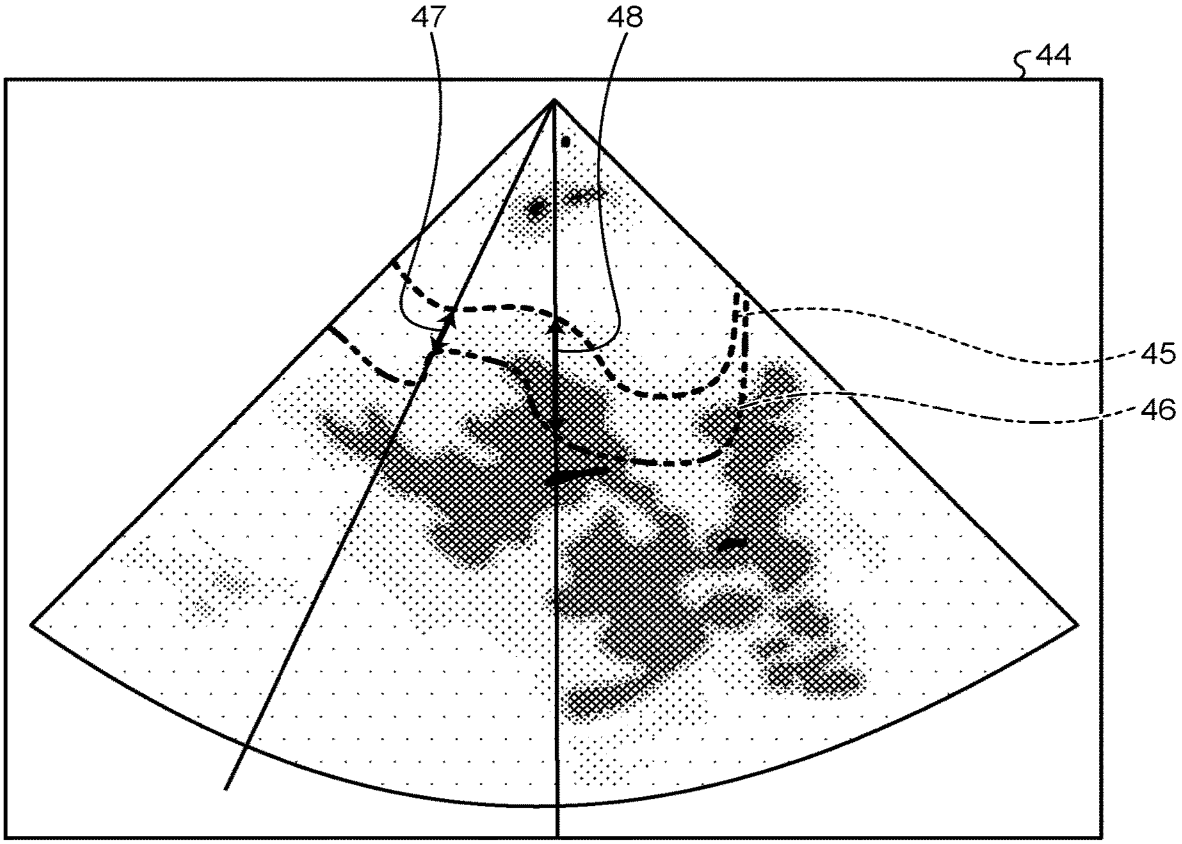
FIG. 12 is a schematic diagram illustrating an example of ultrasonic image data according to the modification.
Figure 13:
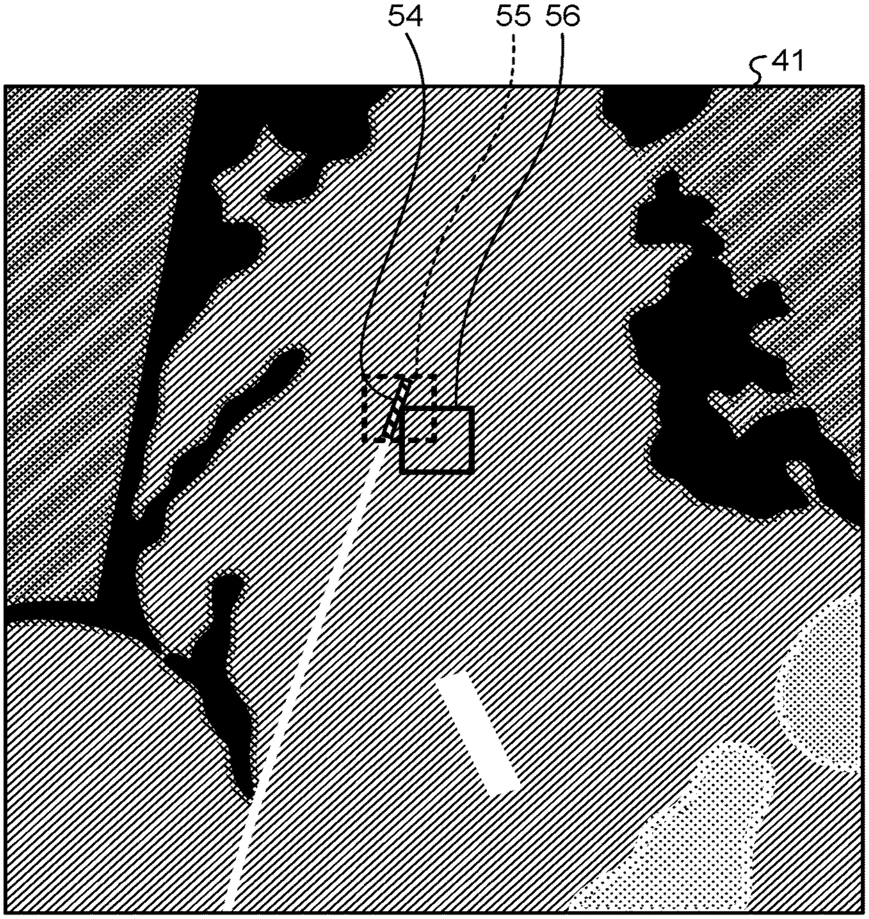
FIG. 13 is a schematic diagram illustrating an example of positional information in which a current position of the object detected on the X-ray image data has been corrected according to the modification.

Although an example has been explained in the above-mentioned embodiment in which an amount of feed of the ICE catheter corresponds to a change in coordinates indicating the leading-end position of the ICE catheter, it is not limited thereto. FIG. 11 is a schematic diagram illustrating an example of an object detected on the X-ray image data according to a modification. FIG. 12 is a schematic diagram illustrating an example of ultrasonic image data according to the modification. FIG. 13 is a schematic diagram illustrating an example of positional information in which a current position of the object detected on the X-ray image data has been corrected according to the modification.

For example, there is a possibility that the ICE catheter or the occlusion catheter bends or swings accidentally in a cardiac cavity due to a pressure by a blood flow caused by a beat regardless of an operation of the robot catheter system 30. In such a case, it is allowable to image the X-ray image data 41 as illustrated in FIG. 3 for one beat, calculate changes against a cardiac phase in coordinates indicating positions of a first leading-end 54 of the ICE catheter and a second leading-end 55 of the occlusion catheter as illustrated in FIG. 11, and make correction by the changes in the coordinates indicating the positions as illustrated in FIG. 13 in synchronization with the electrocardiogram when the current leading-end positions are superimposed.

Furthermore, it is allowable to calculate the changes against a cardiac phase in the coordinates indicating the positions as a fourth vector 47 and a fifth vector 48 based on ultrasonic image data 44 that is obtained by superimposing two pieces of ultrasonic image data representing a largest change in position for one beat generated by the robot catheter system 30 as illustrated in FIG. 12, and make correction by the changes in the coordinates indicating the positions as illustrated in FIG. 13 in synchronization with the electrocardiogram when the current leading-end positions are superimposed.

Sixth Modification

Explained below is the X-ray diagnostic apparatus 10 according to a sixth modification. It will be mainly explained in the sixth modification about differences from the embodiment, and the explanation about the common points will not be repeated. In the explanation about the sixth modification, the same reference signs are assigned to the same parts as the embodiment.

For example, the X-ray diagnostic apparatus 10 according to the sixth modification may perform association for the positional relation between the initial leading-end position of the occlusion catheter on the X-ray image data and the initial leading-end position of the occlusion catheter on the ultrasonic image data. Explained below are functions of the processing circuitry 21 according to the sixth modification.

The acquiring function 211 acquires the ultrasonic image data transmitted by the ultrasonic diagnostic apparatus. More particularly, the acquiring function 211 acquires via the device interface circuitry 25 the ultrasonic image data, which is generated from the signal collected by the transducer inserted into the body of the subject, transmitted by the ultrasonic diagnostic apparatus.

The identifying function 217 identifies initial leading-end positions of the ICE catheter and the occlusion catheter and a direction of the ICE catheter. More particularly, the identifying function 217 identifies a direction of the ICE catheter from the initial leading-end positions of the ICE catheter and the occlusion catheter detected by the detecting function 214 and the X-ray image data collected by the collecting function 213.

Moreover, the identifying function 217 identifies the initial leading-end position of the occlusion catheter on the ultrasonic image data. More particularly, the identifying function 217 identifies the initial leading-end position of the occlusion catheter on the ultrasonic image data from the ultrasonic image data acquired by the acquiring function 211.

Furthermore, the identifying function 217 performs association for the positional relation between the initial leading-end position of the occlusion catheter identified from the X-ray image data and the initial leading-end position of the occlusion catheter identified from the ultrasonic image data.

Figure 14:
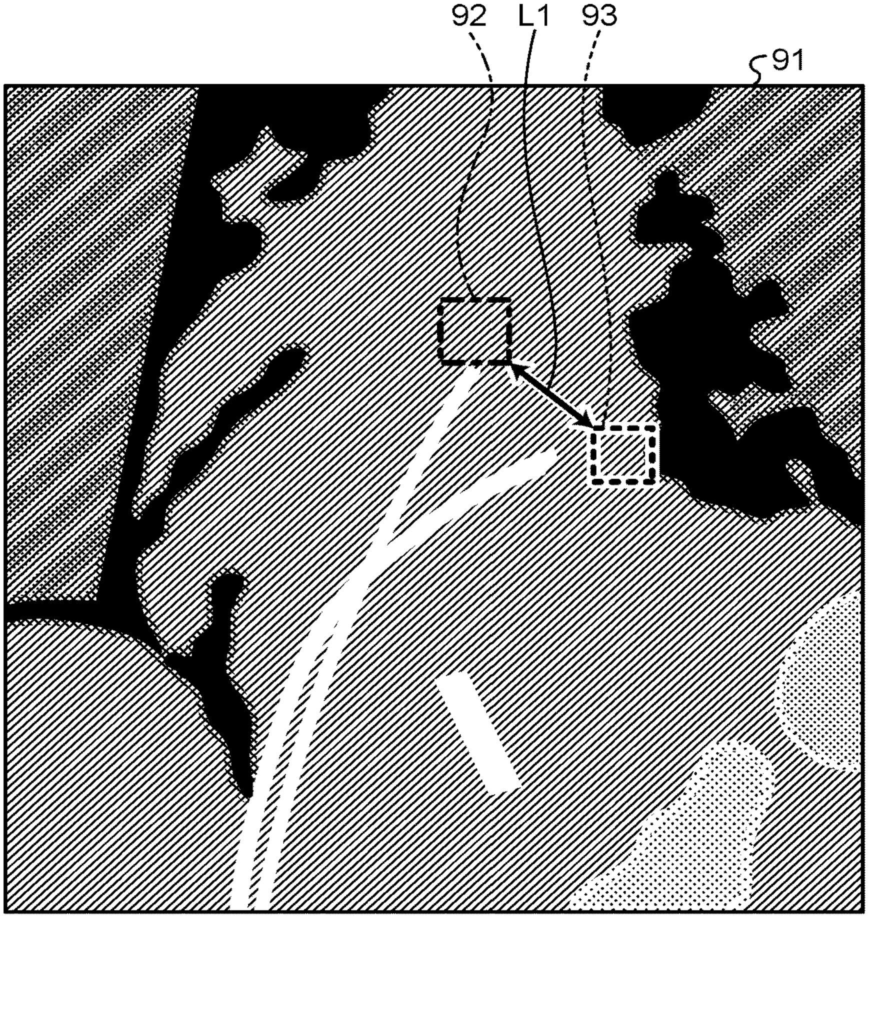
FIG. 14 is a schematic diagram illustrating an example of X-ray image data on which positional information of an object is superimposed according to the modification.
Figure 15:
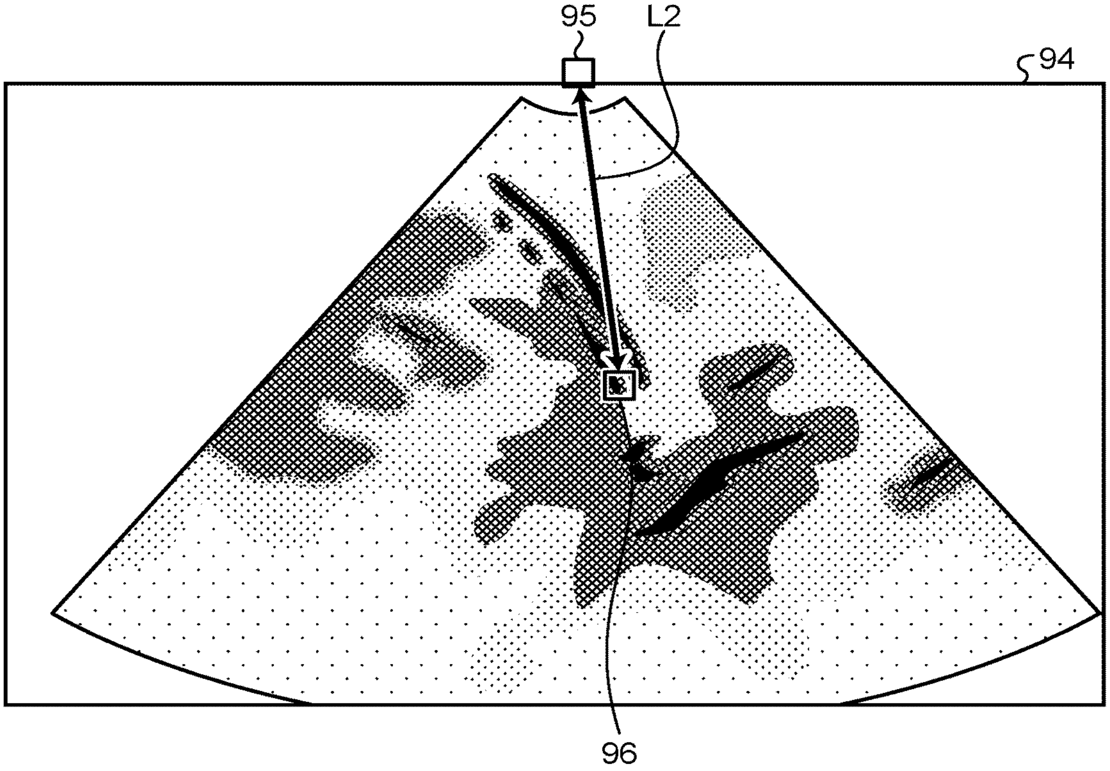
FIG. 15 is a schematic diagram illustrating an example of ultrasonic image data according to the modification.

Explained herein by using FIGS. 14 and 15 is the positional relation, for which the identifying function 217 performs association between the initial leading-end position of the occlusion catheter identified from the X-ray image data and the initial leading-end position of the occlusion catheter identified from the ultrasonic image data.

FIG. 14 is a schematic diagram illustrating an example of the X-ray image data on which the positional information of the object is superimposed according to the sixth modification. FIG. 15 is a schematic diagram illustrating an example of the ultrasonic image data according to the sixth modification. FIG. 14 illustrates initial X-ray image data 91, an ICE catheter 92, and an occlusion catheter 93. FIG. 15 illustrates initial ultrasonic image data 94, a transducer 95, and an occlusion catheter 96.

The identifying function 217 calculates a distance L1 between the ICE catheter 92 and the occlusion catheter 93 from the initial X-ray image data 91 as illustrated in FIG. 14, for example. Moreover, the identifying function 217 calculates a distance L2 between the transducer 95 and the occlusion catheter 96 from the initial ultrasonic image data 94 as illustrated in FIG. 15, for example. The identifying function 217 then links the relation between the calculated distances L1 and L2 and performs association between the apparent distance on the X-ray image data and the distance on the ultrasonic image data.

Figure 16:
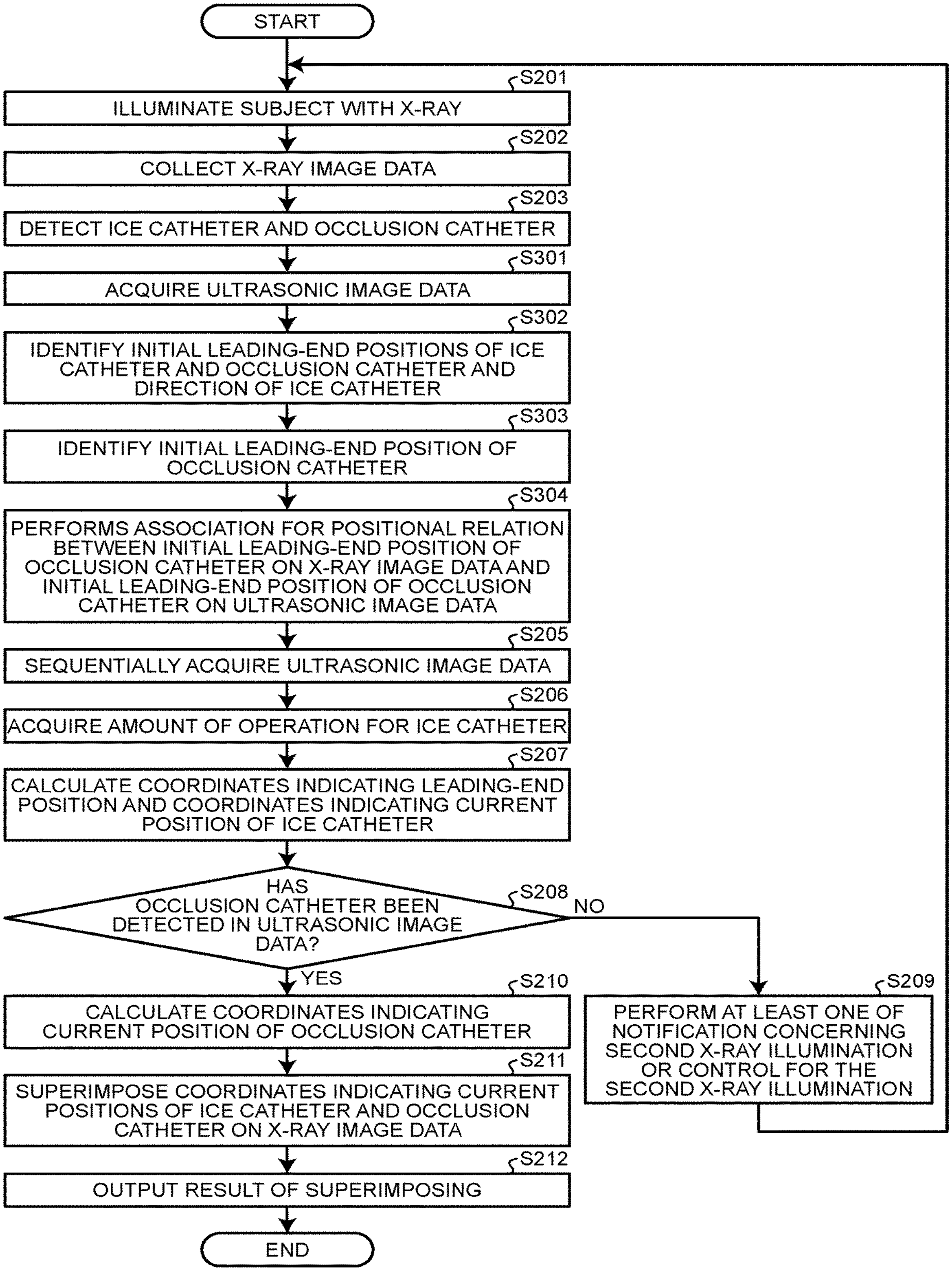
FIG. 16 is a flowchart illustrating an example of processing performed by a robot catheter system according to a modification.

FIG. 16 is a flowchart illustrating an example of processing performed by the robot catheter system according to the sixth modification.

At Step S301, the acquiring function 211 acquires the ultrasonic image data transmitted by the ultrasonic diagnostic apparatus (Step S301). At Step S302, the identifying function 217 identifies initial leading-end positions of the ICE catheter and the occlusion catheter and a direction of the ICE catheter (Step S302).

At Step S303, the identifying function 217 identifies the initial leading-end position of the occlusion catheter on the ultrasonic image data (Step S303). At Step S304, the identifying function 217 performs association for the positional relation between the initial leading-end position of the occlusion catheter identified from the X-ray image data and the position of the occlusion catheter identified from the ultrasonic image data (Step S304).

The X-ray diagnostic apparatus 10 thus can perform association for the positional relation between the initial leading-end position of the occlusion catheter on the X-ray image data and the initial leading-end position of the occlusion catheter on the ultrasonic image data.

Moreover, for example, when a situation is recognized where the ICE catheter bends and there is a possibility that the position of the ICE catheter is incorrect, by performing association for the positional relation between the initial leading-end position of the occlusion catheter identified from the X-ray image data and the position of the occlusion catheter identified from the ultrasonic image data, the X-ray diagnostic apparatus 10 can reduce the fluoroscopy time for X-ray diagnosis in a manipulation in which the robot catheter system and the ICE cooperate together. This can reduce operator's and subject's exposure to X-ray radiation.

Seventh Modification

For example, when the amount of feed for the ICE catheter is equal to or more than a fixed value, the relative positions of the ICE catheter and the occlusion catheter are expected to change. The change in the relative positions can be confirmed from a change in the position of the occlusion catheter on the ultrasonic image data. However, when the position of the occlusion catheter is unchanged on the ultrasonic image data, it is assumed that either the ICE catheter or the occlusion catheter bends inside the blood vessel and fails to move ahead inside the blood vessel. In other words, this event occurs when the ultrasonic image data is unchanged despite movement of the ICE catheter in the robot catheter system 30.

Therefore, when the position of the occlusion catheter is unchanged on the ultrasonic image data despite the operation information being equal to or more than a predetermined amount, the control function 216 performs at least one of a notification concerning second X-ray illumination or a control for the second X-ray illumination. Alternatively, when the position of the occlusion catheter on the ultrasonic image data differs from the associated positional relation despite the operation information being equal to or more than a predetermined amount, the control function 216 may perform at least one of a notification concerning second X-ray illumination or a control for the second X-ray illumination.

Moreover, when acquiring the second X-ray image data, the acquiring function 211 can identify the position of the ICE catheter or the occlusion catheter on that X-ray image, again. The display control function 221 may superimpose, on the X-ray image data, the position of either the ICE catheter or the occlusion catheter that is corrected based on a result of the second identification.

With this configuration, the X-ray diagnostic apparatus 10 can calculate the position accurately even when a bend occurs in either the ICE catheter or the occlusion catheter inside the blood vessel. With this configuration, the operator can perform a manipulation that uses the robot catheter system and the ICE in cooperation. Moreover, the operator can perform a manipulation with less exposure to X-ray than the conventional technologies.

Eighth Modification

Although an example has been explained in the above-mentioned embodiment in which the ultrasonic catheter is an ICE catheter, it may be applied to an intravascular ultrasound (IVUS) catheter as well as the ICE catheter. Features of the ultrasonic catheter in this case include that it is an intravascular catheter and a range of an ultrasonic view is relatively narrow, etc.

Ninth Modification

Because, for example, a range of an ultrasonic view of the ICE catheter is relatively narrow, a target (treatment device or organ) that the operator is observing may be likely to go out of the ultrasonic view area. When the operator moves the treatment device, the treatment device goes out of the ultrasonic view; therefore, it is necessary to move the ICE catheter together with the movement of the treatment device. In this situation, the present invention displays the current position of the ICE catheter with a less exposure to radiation, which can achieve a movement of the ICE catheter while reducing two types of burdens on the subject, exposure to radiation and risk to injure the inside of the body.

Tenth Modification

Although an example concerning a manipulation for a left atrial appendage occlusion has been explained in the above-mentioned embodiment, it may be applied to a treatment support to address a mitral valve or other valves as well as the left atrial appendage occlusion.

It is noted that various data in the present description is typically digital data.

With at least one embodiment of the above-mentioned embodiments, it is possible to perform a manipulation with a lower amount of X-ray used than the conventional technologies.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the scope spirit of the invention as defined by the appended claims.

What is claimed is:

1. An X-ray diagnostic apparatus comprising a processor configured to:
   - sequentially acquire ultrasonic image data generated from a signal collected from a detector of an ultrasonic catheter that is inserted into a body of a subject;
   - collect a plurality of pieces of X-ray image data that are acquired from a plurality of directions;
   - detect the ultrasonic catheter and a treatment device on the X-ray image data;
   - calculate coordinates indicating a current position of the treatment device on the X-ray image data based on operation information about a user operation for the ultrasonic catheter received from a robot catheter system, an opaque marker that is present at a leading end of the treatment device included in an object drawn in the ultrasonic image data, and a result of detection by the detector; and
   - display a first display image that is obtained by superimposing positional information including the coordinates indicating the current position of the treatment device onto the X-ray image data.

2. The X-ray diagnostic apparatus according to claim 1, wherein when the treatment device is not detected in the ultrasonic image data, the processor is configured to perform at least one of a notification concerning second X-ray illumination or a control for the second X-ray illumination.

3. The X-ray diagnostic apparatus according to claim 1, wherein the processor is configured to display positions corresponding to the coordinates indicating the respective current positions including the treatment device and the ultrasonic catheter in a distinguishable manner.

4. The X-ray diagnostic apparatus according to claim 1, wherein the processor is configured to mark and display the positions corresponding to the coordinates indicating the respective current positions of at least one of the treatment device and the ultrasonic catheter.

5. The X-ray diagnostic apparatus according to claim 1, wherein the processor is configured to further superimpose information about a target to be treated that is included in the acquired ultrasonic image data onto the X-ray image data.

6. The X-ray diagnostic apparatus according to claim 1, wherein when acquiring latest X-ray image data, the processor is configured to display a third display image based on the latest X-ray image data.

7. The X-ray diagnostic apparatus according to claim 1, wherein when the position of the treatment device on the ultrasonic image data is unchanged despite the operation information being equal to or more than a predetermined amount, the processor is configured to perform at least one of a notification concerning second X-ray illumination or a control for the second X-ray illumination.

8. The X-ray diagnostic apparatus according to claim 1, wherein the processor is configured to:

identify an initial leading-end position of the treatment device from the X-ray image data, identify an initial leading-end position of the treatment device from the ultrasonic image data, and perform association for a positional relation between the initial leading-end position of the treatment device identified from the X-ray image data and the initial leading-end position of the treatment device identified from the ultrasonic image data.

9. The X-ray diagnostic apparatus according to claim 1, wherein the processor is configured to calculate coordinates indicating a current position of the ultrasonic catheter on the X-ray image data based on the operation information, and display a second display image that is obtained by superimposing positional information including the coordinates indicating the current position of the ultrasonic catheter onto the X-ray image data.

10. The X-ray diagnostic apparatus according to claim 9, wherein the operation information includes at least one of an amount of feed in a direction along a shaft of the ultrasonic catheter or an amount of rotation around the shaft.

11. The X-ray diagnostic apparatus according to claim 10, wherein the processor is configured to detect the detector in the X-ray image data, calculate coordinates indicating an initial leading-end position of the ultrasonic catheter based on a barycenter of the detector, a first directional vector, a second directional vector, and a third directional vector, and calculate the coordinates indicating the current position of the ultrasonic catheter based on the amount of feed in the direction along the shaft of the ultrasonic catheter, the first directional vector, and the initial leading-end position of the ultrasonic catheter.

12. The X-ray diagnostic apparatus according to claim 11, wherein the processor is configured to detect the opaque marker of the treatment device in the X-ray image data, and calculate the coordinates indicating the current position of the treatment device based on an amount of change in the amount of rotation around the shaft of the ultrasonic catheter with respect to the second directional vector, the third directional vector, and the opaque marker.

13. The X-ray diagnostic apparatus according to claim 1, wherein the processor is configured to further superimpose the ultrasonic image data onto the X-ray image data.

14. The X-ray diagnostic apparatus according to claim 13, wherein the processor is configured to change transparency of the ultrasonic image data and further superimpose the transparency-changed ultrasonic image data onto the X-ray image data.

15. An X-ray diagnostic system comprising:

a robot catheter system; and a processor configured to:

sequentially acquire ultrasonic image data generated from a signal collected from a detector of an ultrasonic catheter that is inserted into a body of a subject;

collect a plurality of pieces of X-ray image data that are captured from a plurality of directions and detect the ultrasonic catheter and a treatment device on the X-ray image data;

calculate coordinates indicating a current position of the treatment device on the X-ray image data based on operation information about a user operation for the ultrasonic catheter received from the robot catheter system, an opaque marker that is present at a leading end of the treatment device included in an object drawn in the ultrasonic image data, and a result of detection by the detector; and display a display image that is obtained by superimposing positional information including the coordinates indicating the current position of the treatment device onto the X-ray image data.

16. An X-ray diagnostic method performed by an X-ray diagnostic apparatus, the method comprising:

sequentially acquiring ultrasonic image data generated from a signal collected from a detector of an ultrasonic catheter that is inserted into a body of a subject;

detecting including collecting a plurality of pieces of X-ray image data that are captured from a plurality of directions and detecting the ultrasonic catheter and a treatment device on the X-ray image data;

first calculating including calculating coordinates indicating a current position of the treatment device on the X-ray image data based on operation information about a user operation for the ultrasonic catheter received from a robot catheter system, an opaque marker that is present at a leading end of the treatment device included in an object drawn in the ultrasonic image data, and a result of detection by the detector; and display control including displaying a display image that is obtained by superimposing positional information including the coordinates indicating the current position of the treatment device onto the X-ray image data.

* * * * *